(12) United States Patent
Sharma et al.

(10) Patent No.: US 9,034,400 B2
(45) Date of Patent: May 19, 2015

(54) PROCESS FOR PREPARATION OF A HERBAL EXTRACT

(75) Inventors: Somesh Sharma, Maharashtra (IN); Vijay Singh Chauhan, Maharashtra (IN); Ashish Suthar, Maharashtra (IN)

(73) Assignee: Piramal Enterprises Limited, Mumbai (IN)

( * ) Notice: Subject to any disclaimer, the term of this patent is extended or adjusted under 35 U.S.C. 154(b) by 113 days.

(21) Appl. No.: 13/982,223

(22) PCT Filed: Jan. 27, 2012

(86) PCT No.: PCT/IN2012/000059
§ 371 (c)(1),
(2), (4) Date: Dec. 6, 2013

(87) PCT Pub. No.: WO2012/101657
PCT Pub. Date: Aug. 2, 2012

(65) Prior Publication Data
US 2014/0087012 A1    Mar. 27, 2014

(30) Foreign Application Priority Data
Jan. 28, 2011   (IN) .......................... 246/MUM/2011

(51) Int. Cl.
*A61K 36/42* (2006.01)
*A61K 36/00* (2006.01)
*A61K 9/16* (2006.01)
*A61K 9/20* (2006.01)
*A61K 9/48* (2006.01)

(52) U.S. Cl.
CPC ............. *A61K 36/42* (2013.01); *A61K 2236/31* (2013.01); *A61K 9/1617* (2013.01); *A61K 9/2054* (2013.01); *A61K 9/4866* (2013.01)

(58) Field of Classification Search
CPC ... A61K 26/54; A61K 26/185; A61K 26/886; A61K 2236/31; A61K 2236/51
See application file for complete search history.

(56) References Cited

U.S. PATENT DOCUMENTS

| | | |
|---|---|---|
| 5,098,710 A | 3/1992 | Liu |
| 6,852,695 B2 | 2/2005 | Nag et al. |
| 2002/0151687 A1 | 10/2002 | Khanna |
| 2002/0193310 A1 | 12/2002 | Nag et al. |

FOREIGN PATENT DOCUMENTS

| | | |
|---|---|---|
| CN | 1180545 A | 5/1998 |
| CN | 1303698 A | 7/2001 |
| CN | 1418890 A | 5/2003 |
| CN | 1709900 A | 12/2005 |
| CN | 1858223 A | 11/2006 |
| CN | 1290575 C | 12/2006 |
| CN | 1872134 A | 12/2006 |
| CN | 101366806 A | 2/2009 |
| CN | 101461514 A | 6/2009 |
| CN | 101485429 A | 7/2009 |
| CN | 101597389 A | 12/2009 |
| CN | 101637491 A | 2/2010 |
| GB | 1435664 A | 5/1976 |
| IN | 81887 A1 | 8/1975 |
| IN | 768/MUM/2001 | 8/2001 |
| IN | 231035 | 3/2009 |
| JP | 2005-126370 A | 5/2005 |
| JP | 2006-314273 A | 11/2006 |
| JP | 2008-120701 A | 5/2008 |

OTHER PUBLICATIONS

International Search Report issued in PCT/IN2012/000059 mailed on Jun. 14, 2012 (6 pages).
Lu, Yunn, "Processing and Utilization of Bitter Gourd", Academic Periodical of Farm Products Processing, No. 7, pp. 41-43, 46, Jul. 2006 (4 pages).

*Primary Examiner* — Chris R Tate
*Assistant Examiner* — Russell Fiebig
(74) *Attorney, Agent, or Firm* — Osha Liang LLP

(57) ABSTRACT

A process for preparing an extract of *Momordica charantia*, including: a) preparing crude juice; b) filtering to obtain filtered juice; c) modifying pH; d) allowing the pH modified juice to stabilize; e) neutralizing the stabilized juice; f) allowing the neutralized juice to stand for 20-30 minutes; g) rechecking the pH level; and h) drying the juice to obtain the extract. The process said above is simple, cost effective, which does not employ any harmful organic solvents and which enhances the potency of the constituents. A simple and potent formulation showing anti-diabetic activity comprising active constituents of *Momordica charantia* is also provided.

7 Claims, No Drawings

PROCESS FOR PREPARATION OF A HERBAL EXTRACT

CROSS REFERENCE TO RELATED APPLICATIONS

The present application claims priority to PCT Application No. PCT/IN2012/000059 filed on Jan. 27, 2012, entitled, "Process for Preparation of a Herbal Extract," and incorporated herein by reference in its entirety. PCT Application No. PCT/IN2012/000059 claims priority to Indian Patent Application 246/MUM/2011 filed on Jan. 28, 2011.

FIELD

The present disclosure relates to a process for preparation of a herbal extract powder.

More particularly, the present disclosure relates to a process for preparation of a herbal extract powder from *Momordica charantia*.

BACKGROUND

*Momordica charantia*, is also called bitter melon or bitter gourd. It is a tropical and subtropical vine of the family Cucurbitaceae, widely grown in Asia, Africa and the Caribbean for its edible fruit, which is among the most bitter of all fruits. There are many varieties that differ substantially in the shape and bitterness of the fruit.

Processes for extraction of the active constituents from various parts *Momordica charantia* and the formulations these constituents have been disclosed in Indian Patent 81887, GB1435664, IN156263, U.S. Pat. No. 5,098,710, JP3112999, CN1180545, U.S. Pat. No. 6,852,695, U.S. Pat. No. 6,831,162 IN191582, CN1253734 CN1303698, IN188858, IN826/DEL/2000, IN768/MUM/2001, CN1418890, JP2005126370, CN1562340, CN1858223, JP2006314273, CN1709900, CN1872134, JP2008120701, TW200927139, CN101366806, CN101461514, CN101485429, CN101597389 and CN101637491.

The hitherto reported processes for extraction of the active constituents from various parts *Momordica charantia* suffer from several limitations which include: use of organic solvents for extraction, use of heat during processing, use of enzymes during the extraction process, use of sophisticated equipments for the extraction process.

Also, the formulations comprising the *Momordica* constituents suffer from numerous short-comings which include lower shelf life, reduction in the potency and high cost on account of high processing.

There is therefore felt a need for a process for extraction of the active constituents from *Momordica charantia* which is simple, cost effective, which does not employ any harmful organic solvents and which enhances the potency of the constituents. A need is also felt for a formulation comprising active constituents of *Momordica charantia* which is simple, effective and potent as compared to the existing product.

OBJECT

Some of the objects of the present disclosure are as follows:

It is an object of the present disclosure to provide a process for preparation of an extract of *Momordica charantia* which has a longer shelf life.

It is another object of the present disclosure to provide a process for preparation of an extract of *Momordica charantia* which does not employ any enzymes.

It is still another object of the present disclosure to provide a process for preparation of an extract of *Momordica charantia* which does not employ organic solvents.

It is yet another object of the present disclosure to provide a process for preparation of an extract of *Momordica charantia* which increases the potency of the extract.

It is yet another object of the present disclosure to provide a process for preparation of an extract of *Momordica charantia* wherein the end product is non-hygroscopic.

SUMMARY

In accordance with the present disclosure there is provided a process for preparing an extract of *Momordica charantia* comprising the following steps:
 a) preparing crude juice from crushed and chopped unripe *Momordica charantia* fresh fruit to which water is added intermittently;
 b) filtering the crude juice to obtain filtered juice;
 c) modifying the pH of the juice between 2.5 to 4 pH by adding an organic acid;
 d) allowing the pH modified juice to stabilize by allowing the pH added filtered juice to stand for 5 to 25 minutes;
 e) neutralizing the stabilized juice with the help of alkali;
 f) allowing the neutralized juice to stand for a period of 20 to 30 minutes;
 g) rechecking the pH level of the juice for neutralization; and
 h) drying the neutralized juice to obtain dried extract of *Momordica charantia*.

Typically, the organic acid is at least one selected from the group consisting of citric acid, acetic acid, lactic acid, tartaric acid and oxalic acid.

Typically, the organic acid is citric acid.

Typically, the organic acid is lemon juice.

Typically, the acidic pH is adjusted to a value of 3.8.

Typically, the alkali used for neutralization is at least one alkali selected from the group consisting of sodium hydroxide, potassium hydroxide, calcium hydroxide and sodium bicarbonate.

Typically, the normality of the alkali used for neutralization is in the range of 0.1 N to 4 N.

In accordance with the present disclosure, during the step of neutralization the alkali is added dropwise in the stabilized acidic juice.

In accordance with the present disclosure, the dried extract is obtained by treating the neutralized juice in at least one manner selected from the group consisting of spray drying, vacuum drying and freeze drying to obtain a dried extract of *Momordica charantia*.

There is also provided a formulation containing the dried extract of *Momordica charantia* prepared in accordance with the present disclosure in a dosage form selected from the group consisting of powder, granule, capsule, tablet, sachet, suspension, liquid, pastille, chewing gum, lozenges and pill.

DETAILED DESCRIPTION

In one aspect, the present disclosure provides a process for preparation of a herbal extract powder from *Momordica charantia*. The first and foremost consideration before the commencement of any herbal extraction process is the selection of the particular plant part for the purposes of extraction. Accordingly, the first step in accordance of the process with the present disclosure is selection of the raw material.

In accordance with the process of the present disclosure, fruits are used as the raw material for the extraction process.

Typically, green colored unripe fruits are used as the raw material.

Typically, the fruits that are used as the raw material are fresh.

A crude juice is prepared by crushing and chopping the fruits with intermittent addition of water. The crude juice is then subjected to filtration to obtain a green coloured juice.

A pH modifying agent is added to render the green coloured juice acidic by adjusting the pH to a predetermined value.

Typically, a mild organic acid is used as the pH modifying agent.

Typically, the organic acid is at least one selected from the group consisting of citric acid, acetic acid, lactic acid, tartaric acid, oxalic acid and or the like, or the combinations thereof.

In accordance with one embodiment, citric acid is used as the pH modifying agent. The organic acid used as a pH modifying agent may be obtained from a natural source. Alternatively, the organic acid may be purely synthetic. In one embodiment, lemon juice is used as the pH modifying agent. In another embodiment, citric acid is used as the pH modifying agent.

Typically, the pre-determined pH value is selected from the values selected from the group consisting of 2.5, 3, 3.5 and 4.

In accordance with one embodiment of the disclosure, the predetermined value of pH is in the range of about 3.5 to about 4.0.

In accordance with still another embodiment of the present disclosure, the predetermined value of pH is 3.8.

It is believed that the addition of the organic acids in the clear juice converts the larger/complex proteins of fresh fruits of *Momordica charantia* to small peptide fractions, which help in reduction of blood glucose levels in patients.

The acidic juice extract with a predetermined pH is allowed to stabilize for a period in the range of about 5 min to 25 min, preferably, in the range of about 15 to 20 minutes.

The stabilized acidic juice is neutralized by addition of an alkali to obtain a neutralized juice extract with a pH in the range of about 6.5 to 7.

In accordance with a preferred embodiment of the present disclosure, the pH of the neutralized juice is about 7.

Typically, in the method step of neutralization of the acidic juice using an alkali, after the addition of the alkali to the acidic juice, the neutralized juice is kept aside for a period of about 20 to 30 minutes and the pH is re-checked. If necessary, additional alkali is added to re-adjust the pH in a range of about 6.5 to about 7, preferably about 7.

Typically, the alkali used for the neutralization of the acid juice include but are not limited to sodium hydroxide, potassium hydroxide, calcium hydroxide, sodium bicarbonate or the like, or the combinations thereof.

Typically, the normality of the alkali used for neutralization of the acid juice is in the range of 0.1N to about 4N.

Typically, the alkali is added in a drop-wise manner in the stabilized acidic juice for a time period ranging between 5 to 10 minutes.

Neutralization of acidic juice ensures the prevention of further degradation of peptides in amino acids. Therefore, the fraction prepared from fresh green unripe fruits of *Momordica charantia* (bitter gourd) in accordance with the process of the present disclosure is found to be more potent as compared to the juice obtained from the whole fruit.

The neutralized juice extract thus obtained is dried by at least one manner selected from the group consisting of spray drying, vacuum drying and freeze drying to obtain a dried extract of *Momordica charantia*.

The Polypeptide-p, charantin and bitter constituents of *Momordica charantia* fruits show anti-diabetic activity.

In accordance with another aspect of the present disclosure, there is provided a herbal composition that comprises the dried extract of *Momordica charantia* prepared by the process in accordance with the present disclosure.

Typically, the herbal composition is formulated in a dosage form selected from the group consisting of powder, granule, capsule, tablet, sachet, suspension, liquid, pastille, chewing gum, lozenges and pill.

The present disclosure will now be described with the help of following non-limiting examples.

EXAMPLES

Preparation of *Momordica charantia* Powder

Example 1

5 Kg of fresh unripe green fruits along with seeds of *Momordica charantia* Linn were subjected to cleaning to remove the dust and other superfluous particles from the fruits. The cleaned fruits were chopped and grinded to obtain homologous slurry with the addition of approximately 500 ml of water. The slurry was then filtered to separate the juice by using the nutch filter. The juice was then acidified with 15% of citric acid under continuous stirring to adjust the pH to 4.0. The stirring of juice was continued for 30 minutes and again pH was noted. After stabilization of pH, the pH of acidified juice was then neutralized with help of 15% sodium hydroxide solution to obtain pH to 7.0. The neutralized juice was then subjected to continuous stirring for 30 minutes and pH was once again noted to confirm the pH −7.0. The juice with neutral pH was then concentrated under constant vacuum at 700 mm of Hg at temperature 55° C. to obtained juice with 18 brix (total solid content). The concentrated juice was dried using vacuum dryer adjusted at 60° C. and reduced pressure, which gave 176 gm of the greenish brown coloured free flowing juice powder with characteristic taste and odour.

Analysis of the juice powder showed following constituents in Table 1.

TABLE 1

| Constituents | % by weight |
| --- | --- |
| Proteins | 22.85 |
| Bitters | 3.32 |

Example 2

5 Kg of fresh unripe green fruits along with seeds of *Momordica charantia* Linn were subjected to cleaning to remove the dust and other superfluous particles from the fruits. The cleaned fruits were chopped and grinded to obtain homologous slurry with the addition of approximately 500 ml of water. The slurry was then filtered to separate the juice by using the high speed centrifuge. The juice was then acidified with 15% of citric acid under continuous stirring to adjust the pH to 4.0. The stirring of juice was continued for 30 minutes and again pH was noted. After stabilization of pH, the pH of acidified juice was then neutralized with help of 15% sodium hydroxide solution to obtain pH to 7.0. The neutralized juice was then subjected to continuous stirring for 30 minutes and pH was once again noted to confirm the pH −7.0. The juice with neutral pH was then concentrated under constant vacuum at 700 mm of Hg at temperature 55° C. to obtained juice with 16 brix (total solid content). The concentrated juice was dried using spray dryer at 155° C. inlet temperature, 70° C. to 80° C. outlet temperature, which gave 159 gm of greenish brown coloured free flowing juice powder with characteristic taste and odour. Analysis of the juice powder showed following constituents in Table 2.

TABLE 2

| Constituents | % by weight |
|---|---|
| Proteins | 22.15 |
| Bitters | 2.76 |

Example 3

5 Kg of fresh unripe green fruits along with seeds of *Momordica charantia* Linn were subjected to cleaning to remove the dust and other superfluous particles from the fruits. The cleaned fruits were chopped and grinded to obtain homologous slurry with the addition of approximately 500 ml of water. The slurry was then filtered to separate the juice by using the high speed centrifuge. The juice was then acidified with 15% of oxalic acid under continuous stirring to adjust the pH to 4.0. The stirring of juice was continued for 30 minutes and again pH was noted. After stabilization of pH, the pH of acidified juice was then neutralized with help of 15% Calcium hydroxide solution to obtain pH to 7.0. The neutralized juice was then subjected to continuous stirring for 30 minutes and pH was once again noted to confirm the pH −7.0. The juice with neutral pH was then concentrated under constant vacuum at 700 mm of Hg at temperature 55° C. to obtained juice with 18 brix (total solid content). The concentrated juice was dried using freeze dryer adjusted at −46° C. and reduced pressure, which gave 165 gm of green coloured free flowing juice powder with characteristic taste and odour. Analysis of the juice powder showed following constituents in Table 3.

TABLE 3

| Constituents | % by weight |
|---|---|
| Proteins | 21.33 |
| Bitters | 2.85 |

Preparation of Capsules of *Momordica charantia* 400 mg

Example 4

The juice powder of *Momordica charantia*, microcrystalline cellulose, aerosil, dicalcium phosphate were sifted through 40 US mesh screen, blended and granulated using an aqueous solution of Povidone (PVPK-30). The granules were then dried at temperature of 60±5° C., sifted through 30 US mesh screen, lubricated and filled into hard gelatin capsule shells of suitable size. The capsules had composition as given below in Table 4.

TABLE 4

| Ingredients | Quantity per mg in capsule |
|---|---|
| Juice powder of *Momordica charantia* of example 1 | 400 |
| Microcrystalline cellulose | 100 |
| Aerosil | 3 |

TABLE 4-continued

| Ingredients | Quantity per mg in capsule |
|---|---|
| Dicalcium phosphate | 40 |
| Povidone (PVPK-30) | 5.5 |
| Magnesium stearate | 3 |
| Talc | 3 |
| Sodium starch glycolate | 15 |

Preparation of Granules of *Momordica charantia*

Example 5

The juice powder of *Momordica charantia*, sodium carboxymethyl cellulose, sodium saccharin, citric acid and sodium glycyrrhizinate were sifted through 40 US mesh screen, blended and granulated. The granules were then dried at temperature of 60±5° C., sifted through 30 US mesh screen filled either in bulk or in unit dose per pack.

The granules had composition as given below in Table 5.

TABLE 5

| Ingredients | Quantity in mg |
|---|---|
| Juice powder of *Momordica charantia* of example 1 | 400 |
| Sodium glycyrrhizinate | 10 |
| Sodium citrate | 20 |
| Mint flavour (0.1%) | 1 |
| Sodium carboxy methyl cellulose | 2 |
| Sodium saccharin | 1 |

Preparation of Tablets of *Momordica charantia* Fraction 600 mg

Example 6

The juice powder of *Momordica charantia* of example 1, microcrystalline cellulose, aerosil, dicalcium phosphate were sifted through 40 US mesh screen, blended and granulated using an aqueous solution of Povidone (PVPK-30). The granules were then dried at temperature of 60±5° C., sifted through 30 US mesh screen and lubricated using talc, magnesium stearate and sodium starch glycolate. The lubricated granules were then compressed using suitable die and punches and coated.

The tablets had composition as given below in Table 6.

TABLE 6

| Ingredients | Quantity per mg in tablet |
|---|---|
| Juice powder of *Momordica charantia* of example 1 | 600 |
| Microcrystalline cellulose | 100 |
| Aerosil | 20 |
| Dicalcium phosphate | 50 |
| Povidone (PVPK-30) | 10 |
| Magnesium stearate | 5 |
| Talc | 5 |
| Sodium starch glycolate | 25 |
| Hydroxy propyl methyl cellulose | 8 |
| Titanium dioxide | 5 |
| Propylene glycol | 3 |

Anecdotal Studies:

1) A subject with uncontrolled type II diabetes was administered three capsules of *Momordica charantia* extracts in accordance with the present disclosure per day containing 400 mg extract per capsule; as obtained from Example 4.

It was found that blood glucose level of the subject was reduced to 159 mg/dL from its base level −249 mg/dL during one month of treatment at a dose of one capsule (400 mg) administered three times a day.

2) A test was made of the hypoglycemic effect of the same juice powder of *M. charantia as employed in Example* 4 upon a female patient of 56 years of age and a body weight of 61 kg presenting with non insulin-dependent diabetes. The test subject exhibited a daily blood glucose level of 234 mg/dL, with administration of 500 mg of metformin; BID.

The subject continued administration of the same number of pills of metformin per day and commenced ingestion of 3 hard gelatin capsules containing 400 mg of Juice powder of *M. charantia* per capsule as obtained from example 4 for a period of 90 days. The practiced dosage regimen was 1 capsule before breakfast and 2 capsules before dinner.

The blood analysis of patient showed dramatic effect where the blood glucose level of the subject reduced to 170 mg/dL from its base level −234 mg/dL during a three month of treatment. During the treatment, the patient was on a very moderate diet and she was physically moderately active.

3) A test was made of the hypoglycemic effect of the same juice powder of *M. charantia* as employed in Example 4 upon a non insulin-dependent uncontrolled diabetic male of 61 years of age and a body weight of 67 kg. The subject had long history of diabetes and was on oral medication from more than 5 years. The test subject exhibited a daily blood glucose level of 261 mg/dL, with administration of 500 mg of metformin; three tablets per day.

The subject continued administration of the same number of pills of metformin per day and commenced ingestion of 3 hard gelatin capsules containing 400 mg of Juice powder of M charantia per capsule as obtained from example 4 for a period of 90 days. The practiced dosage regimen was 1 capsule before breakfast and 2 capsules before dinner.

The blood analysis of the patient showed dramatic effect where the blood glucose level of the subject reduced to 159 mg/dL from its base level −261 mg/dL during a three month of treatment.

4) A male subject of 62 years with uncontrolled maturity onset diabetes was administered 3 capsules of commercially available *Momordica charantia* extract per day containing 400 mg of commercial powder per capsule.

It was found that after a period of one month blood glucose level of the subject reduced from a base level of 249 mg/dL to 199 mg/dL consistently.

Thereafter under the same conditions, the subject was administered one capsule as per example 4, three times a day. After one month treatment, the blood glucose level of the subject reduced to 159 mg/dL.

5) A female subject of 70 years with uncontrolled maturity onset diabetes was administered 3 capsules of commercially available *Momordica charantia* extract per day containing 400 mg of commercial powder per capsule.

It was found that after a period of one month, the blood glucose level of the subject reduced from a base level of 265 mg/dL to 215 mg/dL consistently.

Thereafter under the same conditions, the subject was administered one capsule as per example 4, three times a day. After one month treatment, the blood glucose level of the subject reduced to 145 mg/dL.

Safety Profile

No toxic effects or side effects were ascertained in the testings mentioned above. The physical status of examined persons showed no sign of any harmful reaction to treatment. The dosage regimen as well as treatment were patient friendly and well tolerated by diabetics.

Other Benefits:

Besides controlling the blood/urine sugar level the nutraceutical product(s) provide additional benefits in diabetes related human health problems like reduction in fatigue, weakness, drowsiness, numbing effect, frequent urination, unusual thirst and hunger, weight loss, swellings on legs/ankles, burning sensation on feet, palms, relief in skin itching, skin dryness, black patches on skin, hypertension, increase in sleep comfort, energetic feeling, improvement in laziness, blurred vision, frequent skin infections and slow healing of wounds and sores.

A 20-35% reduction in blood glucose doses was also observed after 12 weeks in noninsulin-dependent diabetes mellitus (NIDDM) adult diabetics and can be also used as adjuvant therapy along with oral treatments.

The present disclosure thus provides the specific composition of *Momordica charantia* juice powder, the process for the preparation of juice powder and the medicinal benefits of the same.

Technical advancement: The process for preparation of *Momordica charantia* juice powder and the formulation synthesized in accordance with the present disclosure has the following non-limited advancements:

The present disclosure provides a process for the preparation of a nutraceutical food supplement for diabetics without deteriorating the nutritional and pharmaceutical properties of the natural composition like enrichment of proteins and bitters that are responsible for hypoglycemic activity.

The process for the preparation of *Momordica charantia* juice powder in accordance with the present disclosure is simple and cost effective.

The process for the preparation of *Momordica charantia* juice powder in accordance with the present disclosure is safe as it does not involve use of any harmful solvents.

The *Momordica charantia* juice powder prepared in accordance with the present disclosure is comparatively more effective against diabetes.

The *Momordica charantia* juice powder prepared in accordance with the present disclosure is a natural food which is non toxic, easy to digest with optimum nutrition, health protective and promotive properties.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

Any discussion of documents, acts, materials, devices, articles or the like that has been included in this specification is solely for the purpose of providing a context for the invention. It is not to be taken as an admission that any or all of these matters form part of the prior art base or were common general knowledge in the field relevant to the invention as it existed anywhere before the priority date of this application.

The numerical values given for various physical parameters, dimensions and quantities are only approximate values and it is envisaged that the values higher than the numerical value assigned to the physical parameters, dimensions and quantities fall within the scope of the invention and the claims unless there is a statement in the specification to the contrary.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A process for preparing an extract of *Momordica charantia* comprising the following sequential steps:
  (a) crushing and chopping unripe fresh fruit of *Momordica charantia* to which water is added intermittently to produce a crude juice;
  (b) filtering the crude juice to obtain a filtered juice;
  (c) acidifying the filtered juice to a pH between 2.5 and 4 to produce an acidified juice by adding at least one organic acid selected from the group consisting of citric acid, acetic acid, lactic acid, tartaric acid, oxalic acid and lemon juice;
  (d) stabilizing the pH of the acidified juice by allowing it to stand for 5 to 25 minutes to produce a stabilized juice;
  (e) neutralizing the stabilized juice to produce a neutralized juice by adding at least one alkali selected from the group consisting of sodium hydroxide, potassium hydroxide, calcium hydroxide and sodium bicarbonate;
  (f) allowing the neutralized juice to stand for a period of 20 to 30 minutes;
  (g) rechecking the pH level of the juice for neutralization; and
  (h) drying the neutralized juice to obtain dried extract of *Momordica charantia*.

2. A process as claimed in claim 1, wherein the organic acid is citric acid.

3. The process as claimed in claim 1, wherein the acidic pH is adjusted to a value of 3.8.

4. The process as claimed in claim 1, wherein the normality of the alkali used for neutralization is in the range of 0.1 N to 4 N.

5. The process as claimed in claim 1, wherein during the step of neutralization the alkali is added dropwise in the stabilized acidic juice.

6. The process as claimed in claim 1, wherein the dried extract is obtained by treating the neutralized juice in at least one manner selected from the group consisting of spray drying, vacuum drying and freeze drying.

7. A formulation containing the dried extract of *Momordica charantia* prepared in accordance with claim 1 in a dosage form selected from the group consisting of powder, granule, capsule, tablet, sachet, suspension, liquid, pastille, chewing gum, lozenges and pill.

* * * * *

UNITED STATES PATENT AND TRADEMARK OFFICE
CERTIFICATE OF CORRECTION

| | | |
|---|---|---|
| PATENT NO. | : 9,034,400 B2 | Page 1 of 1 |
| APPLICATION NO. | : 13/982223 | |
| DATED | : May 19, 2015 | |
| INVENTOR(S) | : Somesh Sharma et al. | |

It is certified that error appears in the above-identified patent and that said Letters Patent is hereby corrected as shown below:

In the Claims:

At column 10, claim number 6, line number 23, the words "The process as claimed in claim 1, wherein the dried extract is obtained by treating the neutralized juice in at least one manner selected from the group consisting of spray drying, vacuum drying and freeze drying." should read --The process as claimed in claim 1, wherein the drying of the neutralized juice is selected from the group consisting of spray drying, vacuum drying and freeze drying.--

Signed and Sealed this
Twenty-fourth Day of November, 2015

Michelle K. Lee
*Director of the United States Patent and Trademark Office*